United States Patent

Lenz et al.

[11] Patent Number: 5,852,201
[45] Date of Patent: Dec. 22, 1998

[54] PROCESS FOR THE DISTILLATION OF CRUDE ESTER IN THE DMT/PTA PROCESS

[75] Inventors: Udo Lenz, Recklinghausen; Ulrich Neutzler, Wetter; Anton Schoengen, Witten; Reinhard Sigg, Marl, all of Germany

[73] Assignee: Huels Aktiengesellschaft, Marl, Germany

[21] Appl. No.: 784,519

[22] Filed: Jan. 17, 1997

[30] Foreign Application Priority Data

Apr. 22, 1996 [DE] Germany ................. 196 15 886.9

[51] Int. Cl.$^6$ .................. C07C 67/39; C07C 67/54; B01D 3/00
[52] U.S. Cl. .............. 560/77; 202/158; 203/29; 203/86; 203/91; 203/DIG. 21; 560/78
[58] Field of Search ............... 203/86, 29, 91, 203/DIG. 21, DIG. 6; 202/158; 562/600; 261/112.2; 560/78, 77

[56] References Cited

U.S. PATENT DOCUMENTS

| | | | |
|---|---|---|---|
| 4,235,844 | 11/1980 | Sterzel et al. | 261/112 |
| 5,073,236 | 12/1991 | Gelbein et al. | 203/29 |
| 5,254,719 | 10/1993 | Holzhauer et al. | 560/78 |
| 5,277,878 | 1/1994 | Piotrowski et al. | 261/121.1 |
| 5,419,136 | 5/1995 | McKeigue | 261/94 |
| 5,578,254 | 11/1996 | Mix | 261/112.2 |
| 5,612,067 | 3/1997 | Abrams | 202/158 |

FOREIGN PATENT DOCUMENTS

| | | |
|---|---|---|
| 0 464 046 | 1/1992 | European Pat. Off. . |
| 20 10 137 | 9/1971 | Germany . |
| 30 11 858 | 12/1981 | Germany . |
| 40 26 733 | 2/1992 | Germany . |

OTHER PUBLICATIONS

Ullman vol. 22, 4$^{th}$ Edition, pp. 529–533, G. Hoffmann, et al., "Terephthalsaeuredimethylester" (Dimethyl Terephthalate).

*Primary Examiner*—Virginia Manoharan
*Attorney, Agent, or Firm*—Oblon, Spivak, McClelland, Maier & Neustadt, P.C.

[57] ABSTRACT

A process for preparing crude dimethyl terephthalate, comprises oxidizing a mixture comprising para-xylene and methyl para-toluate, esterifying the oxidized mixture with methanol, separating the resulting crude ester into fractions. By separating the crude ester with a distillation column containing structured packing and using a lower bottom temperature, product yield is increased, and the process is made more economical.

4 Claims, 2 Drawing Sheets

PROCESS FOR THE DISTILLATION OF CRUDE ESTER IN THE DMT/PTA PROCESS

BACKGROUND OF THE INVENTION

1. Field of the Invention

The invention relates to a process for the preparation of crude dimethyl terephthalate (crude DMT) which includes the step of distilling the crude ester in the dimethyl terephthalate/terephthalic acid process.

2. Discussion of the Background

Dimethyl terephthalate (DMT) and terephthalic acid (TA) are prepared industrially in numerous plants all over the world. DMT and TA are important starting compounds for the preparation of polyesters. The fields of application of the polyesters for fibers and films, inter alia, for photographic films and magnetic tapes or bottles made of poly(ethylene terephthalate), to name only a few, have long been known.

It is known that the current Witten-DMT process essentially includes the process steps, oxidation of para-xylene (p-X) and methyl para-toluate (p-TE), generally with downstream off-gas cleaning, esterification with methanol of the reaction products from the oxidation, separation of the resulting so-called crude ester into
  a) a fraction which is recycled to the oxidation,
  b) a crude DMT fraction which contains more than 85% by weight of DMT and
  c) a high-boiling residue fraction, if appropriate workup thereof, for example by methanolysis or thermolysis, and subsequent recovery of the catalyst, purification of the crude DMT fraction, for example by washing, recrystallization and distillation, ("Dimethyl terephthalate", Ullmann Volume 22, 4th edition, pp. 529–533; EP 0 464 046 B1; DE-A 40 26 733). It is also possible to prepare terephthalic acid of appropriate quality from crude DMT fractions which are particularly rich in DMT or from very high purity DMT by specific hydrolysis.

A mixture of para-xylene (p-X) and methyl para-toluate (p-TE or pT ester) is generally oxidized with atmospheric oxygen in the liquid phase in the presence of a heavy metal catalyst (DE-C 20 10 137) at a temperature of about 140° to 180° C. and at a pressure of about 4 to 8 bar absolute. The oxidation stage produces a reaction mixture, which predominantly comprises monomethyl terephthalate (MMT), p-toluyic acid (p-TA) and terephthalic acid (TA), dissolved or suspended in p-TE, and is esterified with methanol at a temperature of about 250° to 280° C. and a pressure of 20 to 25 bar absolute. The resulting crude ester is fractionated by distillation into a p-TE fraction, a crude DMT fraction and a high-boiling catalyst-containing residue fraction. The p-TE fraction is recycled to the oxidation and the crude DMT fraction is converted to the desired product quality via subsequent purification stages. The residue fraction originating from the crude ester distillation is generally subjected to a methanolysis or thermolysis. Processes are also known for recovering and reusing the heavy metal oxidation catalyst from the high-boiling catalyst-containing residues, as are generally produced in the oxidation, esterification or crude ester distillation.

DE-A 30 11 858 discloses a process for the crude ester distillation using a three-column system and further teaches that a low-pressure-drop column is particularly suitable for the TAE distillation, e.g. a column having suitable packing or packing bodies. Such three-column systems require a high capital expenditure.

In the Witten-DMT process, the distillation units used to distill the crude ester are generally the so-called flash chamber system (FIG. 1) and the two-column system (FIG. 2). The columns of these systems are conventionally designed as tray columns. The crude ester is distilled under reduced pressure (vacuum), pressures between 20 and 200 mbar customarily being set at the tops of the columns. Relatively high bottom temperatures result from these operating conditions, which temperatures are generally in the range from 230° to 270° C. It is a disadvantage that undesired side-reactions, for example the formation of so-called high-boilers, occur to an increased extent owing to high bottom temperatures. Although decreasing the pressure in the crude ester distillation could achieve a decrease of the operating temperature in the column bottoms, other disadvantages then occur; increasing the vacuum with constant plant capacity would result in higher gas volumes; columns having correspondingly larger column diameters would be required and thus also a higher capital expenditure would be required. In addition, any decrease in overhead pressures would result in lower condensation temperatures of the distillation vapors arising at the top of the columns. Customarily, the heats of condensation produced at this point are used to produce low- or medium-pressure steam. If the condensation temperature were to be markedly decreased by reducing the pressure in the column tops, the generation of steam can become uneconomic or impossible (condensation temperature <100° C.). This would be disadvantageous for the energy balance over the entire process.

SUMMARY OF THE INVENTION

Accordingly, one object of the present invention is to provide a novel process which enables a crude ester to be distilled as simply and economically as possible.

Another object of the invention is to provide higher yields and improved economics in the Witten-DMT process.

Another object of the invention is to provide gentler distilling conditions in the Witten-DMT process.

These and other objects of this invention have been achieved using structured packing in a crude ester distillation and a gentle procedure, in particular a lower bottom temperature. In this manner, higher yields and thus further improvement of the economics of the Witten-DMT process can be achieved. The present invention gives yield increases of >1%, based on the amount of distilled DMT in comparison with known operating methods.

The first embodiment of the invention relates to a process for purifying a crude ester, which includes:

separating a crude ester into a plurality of fractions with a distillation column containing structured packing;

wherein said column is operated at a bottom temperature of 180°–260° C., and said crude ester contains dimethyl terephthalate.

The second embodiment of the invention relates to a process for preparing crude dimethyl terephthalate, including:

oxidizing a mixture comprising para-xylene and methyl para-toluate, thereby forming an oxidized mixture;

esterifying the oxidized mixture with methanol, thereby forming a crude ester;

separating the crude ester into a plurality of fractions, including:
  (a) a crude dimethyl terephthalate fraction;
  (b) a high-boiling residue fraction; and
  (c) a low-boiling recyclable fraction; wherein said separating is performed with a distillation column containing structured packing; and said column is operated at an overhead temperature of 100°–220° C., at a pressure of 30–200 mbar, and at a bottom temperature of 180°–260° C.; wherein a pressure difference between the top and the bottom of said column is at most 30 mbar.

The third embodiment of the invention relates to an apparatus, including:

a distillation column containing structured packing in contact with a crude ester which contains dimethyl terephthalate.

DETAILED DESCRIPTION OF THE PREFERRED EMBODIMENT

At the outset, FIGS. 1 and 2 will be described in more detail with a legend for each.

Figure 1:
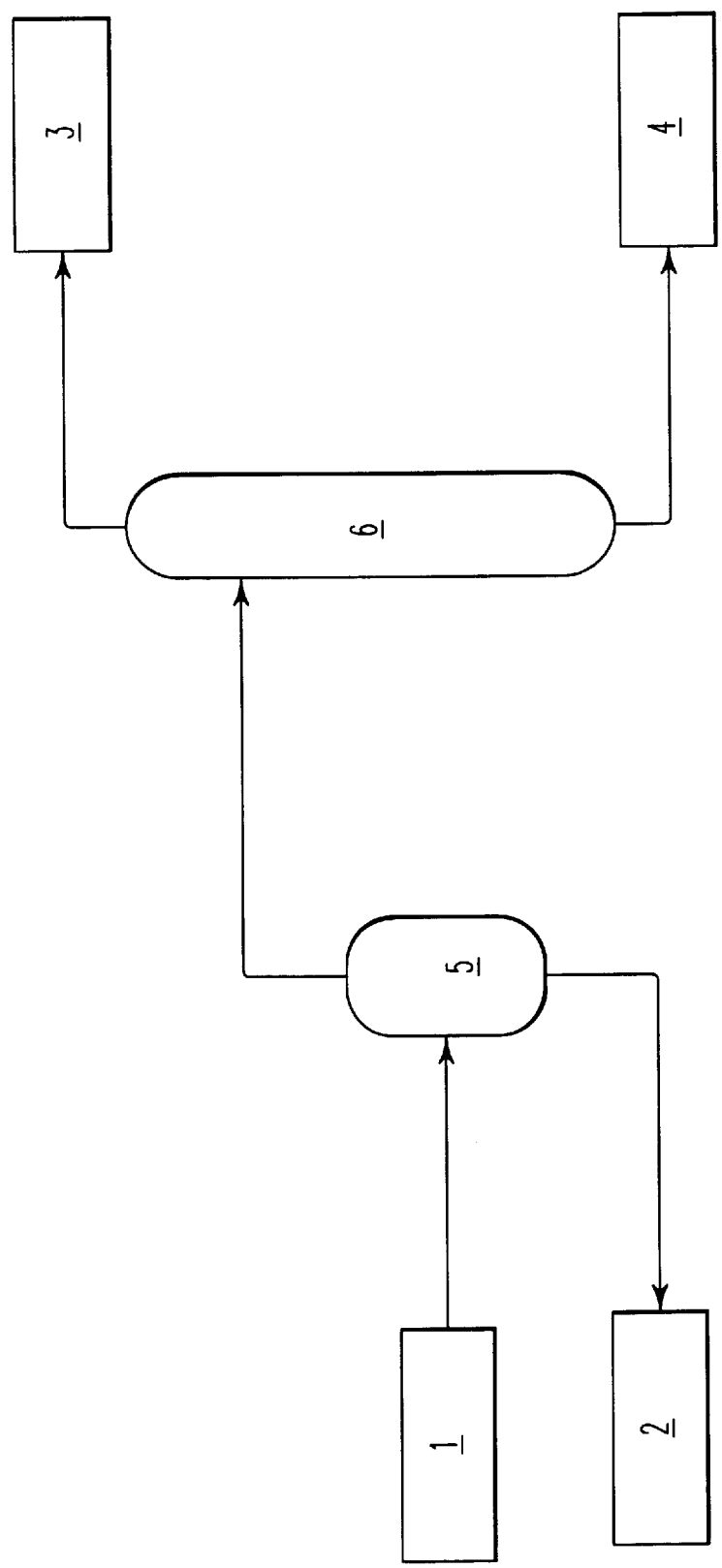
FIG. 1 illustrates a block diagram of a crude ester distillation in the DMT process, which is termed a flash chamber system.

Legend to FIG. 1

FIG. 1 shows a block diagram of a crude ester distillation in the DMT process, which is termed a flash chamber system:

| | Material streams |
|---|---|
| 1 | Crude ester from the esterification |
| 2 | High-boiling, catalyst-containing residue fraction for workup |
| 3 | Recycle of the p-TE fraction to the oxidation |
| 4 | Crude DMT for further purification |
| | Plant components |
| 5 | Flash chamber |
| 6 | Crude ester distillation column |

Figure 2:
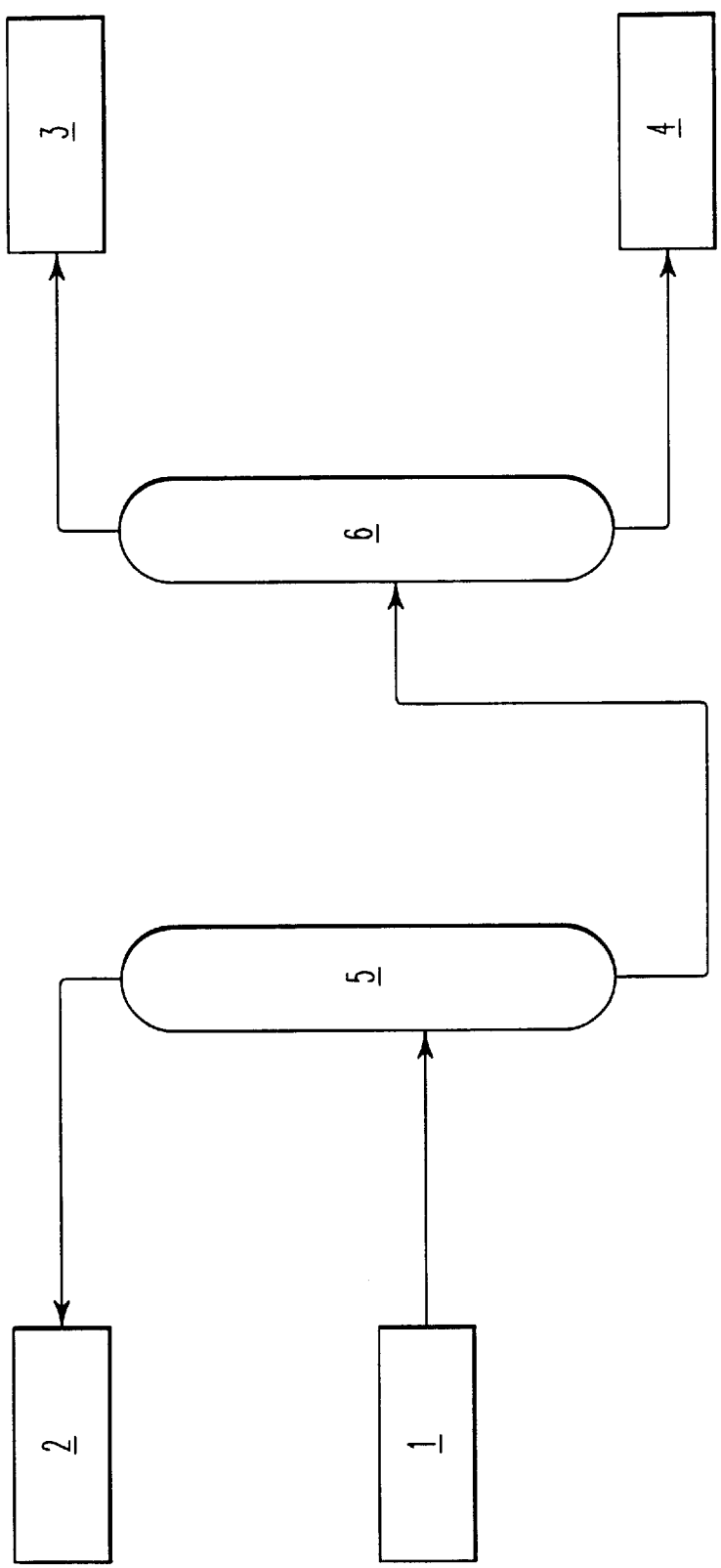
FIG. 2 illustrates a block diagram of a crude ester distillation in the DMT process, which is termed a two-column system.

Legend to FIG. 2

FIG. 2 shows a block diagram of a crude ester distillation in the DMT process, which is termed a two-column system,

| | Material stream |
|---|---|
| 1 | Crude ester from the esterification |
| 2 | Recycle of the p-TE fraction to the oxidation |
| 3 | Crude DMT fraction for further purification |
| 4 | High-boiling, catalyst-containing residue fraction for workup |
| | Plant components |
| 5 | p-TE distillation column |
| 6 | Crude DMT distillation column |

4 High-boiling, catalyst-containing residue fraction for workup

Plant components 5 p-TE distillation column

6 Crude DMT distillation column

Legend of abbreviations:

| | |
|---|---|
| p-X | para-xylene |
| p-TA | para-toluic acid |
| p-TE | methyl para-toluate (pT ester) |
| BME | methyl benzoate |
| HM—BME | methyl hydroxymethyl benzoate |
| MM—BME | methyl methoxymethyl benzoate |
| DMT | dimethyl terephthalate |
| DMT-crude | crude ester (DMT crude ester stream following esterification) |
| crude DMT | dimethyl terephthalate fraction following crude ester distillation |
| high-purity DMT | high-purity dimethyl terephthalate (high-purity DMT intermediate or end product) |
| DMO | dimethylorthophthalic acid |
| DMI | dimethylisophthalic acid |
| DMP | dimethyl phthalates = isomeric mixture of DMT, DMO and DMI |
| MMT | monomethyl terephthalate (terephthalic acid monomethyl ester) |
| TA | terephthalic acid |
| MTA | medium-purity terephthalic acid |
| PTA | high-purity terephthalic acid |
| PTA-p | terephthalic acid of very high purity, i.e. superpure (content of MMT and p-TA together < 50 ppm by weight) |
| TAS | terephthalaldehydic acid (4-CBA) |
| TAE | methyl terephthalaldehydate |

Other features of the invention will become apparent in the course of the following descriptions of exemplary embodiments which are given for illustration of the invention and are not intended to be limiting thereof.

Preferably, in the process of the invention, the distillation column is operated at an overhead temperature ranging from 100° to 220° C., at a pressure of 30 to 200 mbar and a bottom temperature between 180° to 245° C.; more preferably at a bottom temperature in the range from 190° to 230° C. These ranges include all specific values and subranges therebetween.

More preferably, in the process of the invention, the distillation column is operated at an overhead temperature ranging from 100° to 180° C.; and most preferably from 100° to 140° C. These ranges include all specific values and subranges therebetween, including 105°, 110°, 120°, 130°, 150°, 160°, and 170° C.

More preferably, in the process of the invention, the distillation column is operated at pressures ranging from 30 to 180 mbar; more particularly preferably from 30 to 160 mbar; and most preferably from 30 to 140 mbar. These ranges include all specific values and subranges therebetween, including 35, 40, 60, 100, 120, 130, 150, and 170 mbar.

More particularly preferably, in the process of the invention, the distillation column is operated at a bottom temperature ranging from 190° to 230° C.; and most particularly preferably from 200° to 220° C. These ranges include all specific values and subranges therebetween, including 195°, 205°, 215°, and 225° C.

More preferably, in the process of the invention, the respective pressure difference between column top and column bottom should not exceed 20 mbar; and more particularly preferably 15 mbar. These ranges include all specific values and subranges therebetween, including 19, 18, 17, 16 and 15.1.

Preferably, in the process of the invention, the crude ester is distilled in a two-column system, or in a flash chamber system. The crude ester may be distilled in a continuous process or in a batch process.

In the present invention, structured packing includes ordered separation units in which the alternating arrangement of the individual structural elements form open, crossing channels. These structural elements may be either helical or lamellar in nature, or a combination of both. Structural elements of this type can be, e.g., shaped or perforated metal sheets or plates, expanded metal, wire gauze, wire cloth, or ceramic or plastic moldings. Special structured packing of this type is offered, inter alia, by SULZER AG, Switzerland. The structured packing may also include structural elements such as embossed metal, lanced metal, or corrugated metal elements.

In the present invention, structured packing also includes structured packing which essentially contain no horizontally orientated structural elements. That is, the structured packing preferably contains non-horizontally-oriented or vertically-oriented structural elements. The catalyst present in the crude ester has a tendency in general to crystallize out and form solids, this can affect the known systems for crude ester distillation. By avoiding any horizontal surfaces in the process of the invention, the formation and settling of deposits which can lead to blockage and thus breakdown of the entire crude ester distillation are avoided. In the process of the invention, structured packing having the lowest possible liquid holdup is preferably used. This is a considerable advantage in comparison with packing made of packing bodies and valve trays of known types.

In the process of the invention, structured packing of stainless steels or other corrosion-resistant materials is preferably used; in particular structured packing of aluminum, Hastelloy, titanium, or plastic, for example Teflon, or ceramic, such as Al-silicate. There may be single or multiple packing beds.

Preferably, in the present invention, structured packing has a surface area ranging from 100 to 800 $m^2/m^3$. It is more preferable that structured packing has a surface area ranging from 200 to 700 $m^2/m^3$; more particularly preferably from 300 to 600 $m^2/m^3$; and most preferably from 400 to 500 $m^2/m^3$. These ranges include all specific values and subranges therebetween, including 105, 110, 125, 150, 175, 225, 250, 275, 325, 350, 375, 425, 450, 475, 525, 550, 575, 625, 650, 675, 725, 750, and 775 $m^2/m^3$.

The void fraction of the structured packing of the present invention is not particularly limiting. However, in the present invention, the structured packing may have a void fraction greater than 0.1; preferably greater then 0.3; more preferably greater then 0.5; more particularly preferably greater than 0.7; most preferably greater than 0.8; and most particularly preferably greater than 0.9. These ranges include all specific values and subranges therebetween, including 0.65, 0.75, 0.85, 0.91, 0.92, 0.93, 0.94, 0.95, 0.96, 0.98, and 0.99.

In addition, further advantages can be gained by the process of the invention if structured packing is used which has a surface which avoids deposits and adhesions. For example, materials with particularly smooth surfaces can be used. Teflon or materials which are similar to Teflon in their relevant action may also be used. Low surface energy materials are particularly preferred.

At predetermined overhead temperatures, the process according to the invention provides a crude ester distillation that is economically more efficient and gentler on the product. In addition to the marked improvement in the economic efficiency, the invention reduces the tendency toward deposits in the crude ester distillation to a greater extent than the processes known to date.

Having generally described this invention, a further understanding can be obtained by reference to certain specific examples which are provided herein for purposes of illustration only and are not intended to be limiting unless otherwise specified.

EXAMPLE

Operational practice shows that at a given residence time and a bottom temperature of approximately 260° C. in the flash chamber, cf. FIG. 1, approximately 8.6% of high-boilers, based on the amount of DMT distilled, are newly formed and, by known processes, in the most favorable case, 50% of the high-boilers formed can be converted back into products of value (e.g. in a methanolysis). The loss in yield here is thus around 4.3%.

In an experiment, a crude ester, after installing the structured packing, was then distilled at a bottom temperature of 190° C. under gentle conditions according to the present invention. In the experiment, the losses due to formation of high-boilers were only 5.4%, based on the DMT present in the crude ester. At a reconversion rate of 50%, a loss in yield of only 2.7% remains.

Installing the structured packing and using the lower bottom temperature in the crude ester distillation thus markedly improves the economic efficiency of the process. This corresponds to an increase in yield, in comparison with the known flash chamber procedure, of 1.6%, based on the amount of DMT distilled in the crude ester.

The entire contents of German patent application 19615886.9, filed Apr. 22, 1996, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing crude dimethyl terephthalate, comprising:

oxidizing a mixture comprising para-xylene and methyl para-toluate, thereby forming an oxidized mixture;

esterifying the oxidized mixture with methanol, thereby forming a crude ester;

separating the crude ester into a plurality of fractions, comprising:

(a) a crude dimethyl terephthalate fraction;

(b) a high-boiling residue fraction; and (c) a low-boiling recyclable fraction; wherein said separating is performed with a distillation column comprising structured packing; and said column is operated at an overhead temperature of 100°–220° C., at a pressure of 30–200 mbar, and at a bottom temperature of 180°–260° C.; wherein a pressure difference between the top and the bottom of said column is at most 30 mbar.

2. The process of claim 1, wherein said high-boiling residue fraction comprises catalyst; and said low-boiling recyclable fraction comprises methyl para-toluate.

3. The process of claim 1, further comprising recycling said low-boiling recyclable fraction back into said oxidizing.

4. The process of claim 3, wherein said oxidizing, said esterifying, said separating, and said recycling are continuous.

\* \* \* \* \*